United States Patent
Olejniczak

[11] Patent Number: 6,150,951
[45] Date of Patent: Nov. 21, 2000

[54] MEDICAL TELEMETRY SYSTEM WITH WIRELESS AND PHYSICAL COMMUNICATION CHANNELS

[75] Inventor: Stefan Olejniczak, Stuttgart, Germany

[73] Assignee: Hewlett-Packard, Fort Collins, Colo.

[21] Appl. No.: 09/178,311

[22] Filed: Oct. 23, 1998

[30] Foreign Application Priority Data

Dec. 22, 1997 [EP] European Pat. Off. ............. 97122622

[51] Int. Cl.[7] .................................................. H01H 67/00
[52] U.S. Cl. .................... 340/825.03; 128/903; 455/509; 607/60
[58] Field of Search ............... 128/903; 607/60; 340/10.51, 10.2, 825.03; 455/509, 515, 516

[56] References Cited

U.S. PATENT DOCUMENTS

| | | | |
|---|---|---|---|
| 5,311,449 | 5/1994 | Adams | 607/9 |
| 5,438,329 | 8/1995 | Gastouniotis et al. | |
| 5,839,075 | 11/1998 | Haartsen et al. | 455/509 |

FOREIGN PATENT DOCUMENTS

| | | |
|---|---|---|
| 0280196A2 | 8/1988 | European Pat. Off. |
| 0735498A1 | 10/1996 | European Pat. Off. |
| WO97/18639 | 5/1997 | WIPO |

*Primary Examiner*—Carl H. Layno

[57] ABSTRACT

A telemetry system comprising a transmitter for transmitting signals, preferably electromagnetic signals, and a receiver for receiving the signals from the transmitter. The receiver comprises a receiver contact unit for providing a contact with a transmitter contact unit of the transmitter. The receiver contact unit and the transmitter contact unit are adapted to provide a data communication during a contact phase for assigning a transmission channel to the transmitter and/or to the receiver. The receiver may further include apparatus for monitoring a transmission activity in a pre-given channel range for determining possible channels in use, so that the transmission channel is assigned to the transmitter in accordance with the determined channels in use. The telemetry system according the invention is preferably used to for medical applications, such as pulsoximetry or electrocardiography.

16 Claims, 1 Drawing Sheet

MEDICAL TELEMETRY SYSTEM WITH WIRELESS AND PHYSICAL COMMUNICATION CHANNELS

BACKGROUND OF THE INVENTION

The present invention relates to telemetry systems in general, and more particularly to telemetry systems for medical purposes.

Telemetry is generally defined as a (more or less automated) communications process by which measurements are made and/or other data collected at remote or inaccessible points, and transmitted to a receiving equipment for monitoring, display, and/or recording. Originally, the information was sent over wires, but modern telemetry systems more commonly use radio transmission. Basically, the communication process is the same in either case. Among the major applications are monitoring electric-power plants, gathering meteorological data, monitoring manned and unmanned space flights, and more and more medical applications such as pulsoximetry or electrocardiography.

Telemetry systems normally comprise a transmitter for transmitting electromagnetic signals, e.g. from a measurement, and a receiver for receiving the electromagnetic signals from the transmitter. In current medical telemetry systems, the transmitter is usually carried by the patient and the receiver is typically installed in an operator room. Large systems may have a multitude of transmitters and receivers.

Each transmitter normally operates with a corresponding receiver on a certain channel, preferably over a pre-defined carrier frequency. Those channels, e.g. RF channels, are usually fixed programmed by the manufacturer. RF channels are related to RF carrier frequencies (e.g., in narrowband FM systems) or to coding (spreading) sequences in spread spectrum systems (e.g., direct sequence or frequency hopping systems). It is to be understood that the term 'channel' is used herein in a very general sense and shall mean any communication channel which can be implemented by various technologies as known in the art, and is neither limited e.g. to certain fixed frequencies, nor to a certain transmission medium, or the like.

The currently available telemetry systems exhibit certain drawbacks:

The matching of each transmitter/receiver pair has to be identified by the operator. This is generally carried out by labeling each, transmitter and receiver, with the same channel number.

In order to provide maintenance and application service, the channels must be tracked during their production process, throughout the entire ordering and service process, and at their place of application, such as a hospital. This leads to increased administration effort. However, in case that the channel assignment gets lost for certain reasons, it will become very difficult or even impossible to reassign the channel and to carry out certain services.

If either the transmitter or the receiver fails or becomes inoperable for other reasons, that specific channel cannot be used anymore, since it is unique for each pair of transmitter and receiver. The channel is occupied until the component becomes operative again. Since the transmitter's battery is the most likely part to fail, this leads to designs, where the battery must be exchangeable by the operator.

A solution as known in the art for at least resolving some of the drawbacks is to provide a plurality of channels for the communication between the receiver and the transmitter(s), which can be manually selected for a specific transmitter/receiver pair.

SUMMARY OF THE INVENTION

It is an object of the invention to provide an improved telemetry system.

A telemetry system according to the invention comprises a transmitter for transmitting signals, preferably electromagnetic signals, and a receiver for receiving the signals from the transmitter. The receiver comprises a receiver contact unit for providing a contact with a transmitter contact unit of the transmitter. The receiver contact unit and the transmitter contact unit are adapted to provide a data communication during a contact phase for assigning a transmission channel to the transmitter and/or to the receiver.

The invention breaks up a fixed assignment of transmitter and receiver by introducing a communication between the two, thus allowing the transmitter channel being programmed by the receiver or the receiver channel being programmed by the transmitter.

In a preferred embodiment, the receiver further comprises means for monitoring a transmission activity in a channel range for determining channels in use. A transmission channel is assigned to the transmitter in accordance with the determined channels in use.

In another embodiment, the receiver is adapted to physically receive the transmitter, e.g., as a base station. Physically receive shall mean any kind of mechanically taking up, picking up, absorbing, or otherwise providing corresponding fixtures, slots, or the like.

In a further embodiment, the receiver contact unit and the transmitter contact unit respectively comprise corresponding components for establishing and providing—during the contact phase—a communication therebetween preferably electrically or inductively or by an infrared, radio or ultrasound link, whereby the communication can be unidirectional or bidirectional.

The telemetry system according to the invention is preferably used for medical applications, such as such as pulsoximetry or electrocardiography.

A method according to the invention for assigning transmission channels in a telemetry system comprises a step of providing—during a contact phase—a data communication between the transmitter and the receiver for assigning a transmission channel to the transmitter and/or to the receiver.

In a preferred embodiment, the method further comprises the steps of monitoring a transmission activity in a channel range for determining channels in use, and during the contact phase, providing a data communication between the transmitter and the receiver for assigning a transmission channel to the transmitter in accordance with the determined channels in use.

In another embodiment, the receiver further transfers to the transmitter—during the contact phase—a unique transmitter identity code for the transmitter, and/or a receiver identity code of the receiver, and/or information about a standby mode of the transmitter, and/or personal information such as information about a person who will receive or carry the transmitter.

In case that the receiver has assigned and transferred a unique transmitter identity code for the transmitter, the transmitter may transmit—during an operation thereof—the transmitter identity code and other data on the assigned channel to the receiver. The receiver performs a substantially ongoing check of the received transmitter identity code for determining whether a signal received by the receiver on the respective channel originates from the transmitter.

It is to be understood, that the scanning phase and the contact phase need not necessarily be consecutive time periods, but may also overlap or the scanning phase might even comprise the contact phase.

BRIEF DESCRIPTION OF THE DRAWINGS

Other objects and many of the attendant advantages of the present invention will be readily appreciated and become better understood by reference to the following detailed description when considering in connection with the accompanied drawing FIG. 1, which shows a preferred embodiment of a telemetry system according to the invention.

DETAILED DESCRIPTION OF THE INVENTION

Figure 1:
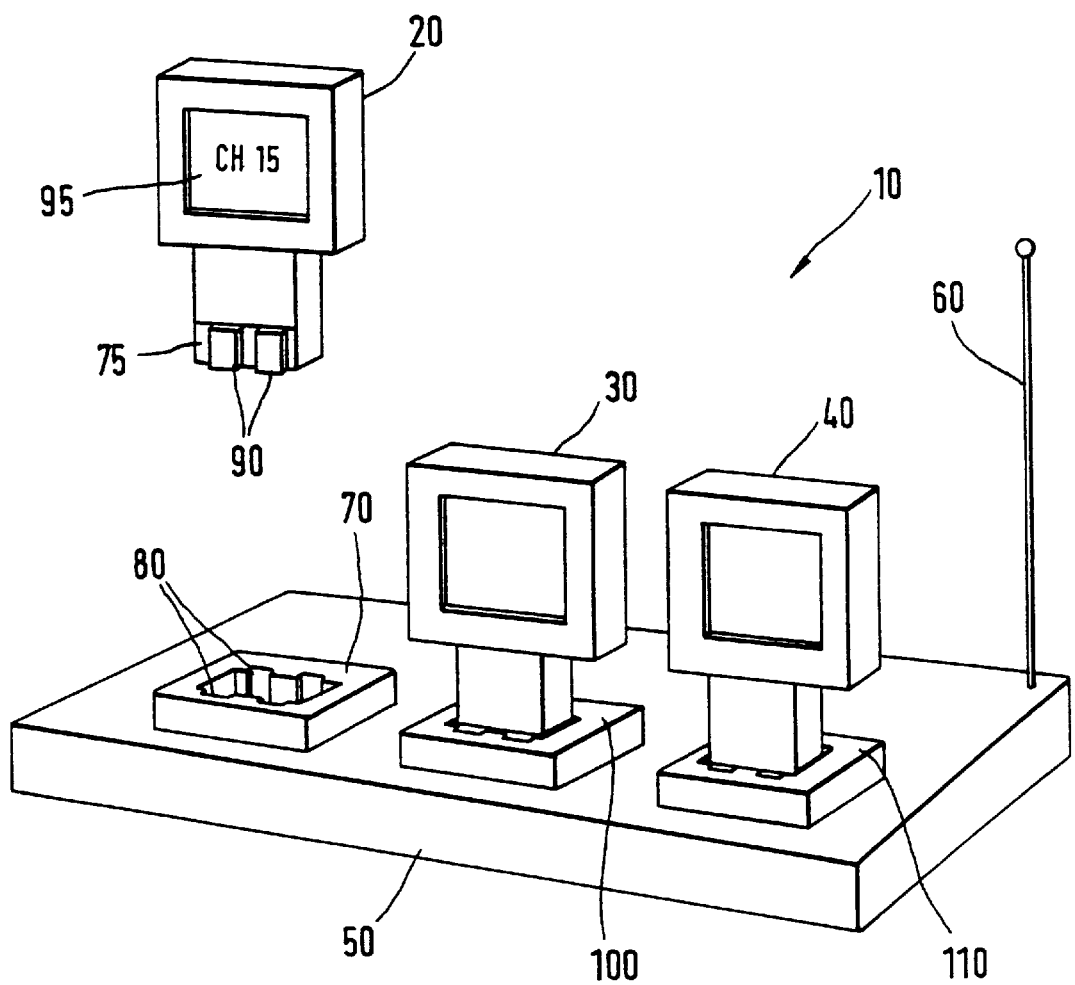

FIG. 1 shows a preferred embodiment of a telemetry system 10 according to the invention. The telemetry system 10 comprises at least one transmitter 20, and preferably a plurality of further transmitters 30 and 40. The embodiment shall be explained in the following for the example of three transmitters 20 to 40, however, it is to be understood that the number of transmitters in the telemetry system 10 is not limited to a certain number. The telemetry system 10 further comprises a receiver 50, which is preferably adapted to physically receive the plurality of transmitters 20 to 40, e.g., in sense of a base station.

The transmitters 20 to 40—when operated—respectively transmit information (e.g. from a specific application such as measurement or monitoring purposes) via specific antennas (not shown in FIG. 1) to the receiver 50, which receives the signals, e.g., by an antenna 60. The transmitters 20 to 40 preferably transmits that information as electromagnetic signals. However, other transmission signals as known in the art such as ultrasonic or infrared can be used. The receiver 50 might process or further transmit the received information. In a medical application, the transmitters 20 to 40 preferably transmit biomedical information.

The operation of the transmitters will be explained in the following for the example of transmitter 20. Before transmitter 20 will be used for transmission purposes in combination with the receiver 50, the receiver 50 monitors the "on air activity" in its environment for any transmission activity in a certain channel range assigned to the receiver 50. This phase is also called "scanning phase". The receiver 50 thus determines which channels are in use, e.g., by any other transmitter or by other functional units. In a preferred embodiment, the receiver 50 comprises a synthesizer receiver unit for stepping through a predefined channel range and for measuring the received signal strength on each one of the channels. When the received signal strength of a certain channel exceeds a certain predefined value, the receiver 50 will treat this channel as being in use.

In order to prepare the transmitter 20 for transmission purposes in combination with the receiver 50, the transmitter 20 will be brought 'in contact' with the receiver 50. This phase is also called "contact phase". The receiver 50 therefore comprises a receiver contact unit 70 for providing the contact with a transmitter contact unit 75 of the transmitter 20. During the contact phase, a data communication takes place between the receiver 50 and the transmitter 20 (to be prepared for use) by means of the contact units 70 and 75. The contact units 70 and 75 respectively comprise corresponding components for establishing and providing a communication therebetween by any means and ways as known in the art, such as electrically or inductively or by an infrared, radio or ultrasound link, whereby the communication can be either unidirectional or bidirectional.

In a preferred embodiment as shown in FIG. 1, the receiver contact unit 70 comprises one or more contact areas 80 and the transmitter contact unit 75 comprises one or more contact areas 90, which—when brought into contact—establish a direct electrical contact between the contact units 70 and 75. It is clear that the contact areas 80 and 90 are represented in FIG. 1 only schematically and may comprise a plurality of individual contacts, e.g., as known from serial or parallel computer interfaces.

During the contact phase, the receiver 50 transfers information to the transmitter 20, which indicates a free channel to be used by the transmitter 20 for communicating with the receiver 50. The free channel has been selected by the receiver 50 during a past scanning phase which might still endure. Additionally, the receiver 50 may transfer a unique transmitter identity (ID) code for the transmitter 20 and other data, such as an ID code of the receiver 50, information about a standby mode, personal information e.g. about the person who will receive or carry the transmitter 20 for a medical application, to the transmitter 20. The transmitter 20 preferably acknowledges a valid reception of the received data, e.g., by echoing or the like.

In one embodiment, the transmitter 20 has been programmed to a specific channel, e.g., during a manufacturing process. During the contact phase between the transmitter 20 and the receiver 50, the transmitter 20 re-programs the receiver 50 by indicating the channel to be used for communicating with the receiver 50. In that case, the contact phase can be executed without executing a scanning phase before.

After the contact phase, the transmitter 20 may be removed from the receiver 50 and the contact units 70 and 75, e.g. the contact areas 80 and 90, will be separated. The transmitter 20 is now ready for operation and might start transmitting to the receiver 50.

In case that the receiver 50 has assigned and transferred a unique transmitter ID code for the transmitter 20, the transmitter 20 will transmit—in operation—the ID code and other data, e.g. patient data in a medical application, on the assigned channel. The receiver 50 performs a substantially ongoing check of the received transmitter ID code, and can thus determine whether a received signal on the respective channel originates from the transmitter 20. This allows to detect any other transmitter or other source, which might be (accidentally) operating on the same channel, so that the signal can clearly be identified as originating from the transmitter 20. In particular in medical applications, it is essential that the received information can be clearly assigned to a specific patient. In case the receiver 50 detects other activities on the channel assigned to the transmitter 20, the receiver 50 will preferably initiate an alarm or other adequate steps or measures.

The transmitter 20 and/or the receiver 50 may contain a display or other means for making information visible. This allows to display certain information such as a number of the selected channel, the ID code(s), or the personal information transferred from the receiver 50, thus giving the operator useful feedback about the 'programming' of the transmitter 20 and/or whether the programming has been successful. In medical applications, the display may show the patient's name or a bed label, coming e.g. from a central station via a network into the receiver 50 and therefrom to the transmitter 20. In FIG. 1, the transmitter 20 comprises a display 95 indicating as an example a channel number "CH 15" as the channel number selected by the receiver 50 for the transmitter 20.

In a specific embodiment, the transmitter 20 can be manually shut down or brought into a standby mode, e.g., by short contacting (e.g. for a defined period of time such as less than two seconds) the contact areas 80 and 90 of the receiver 50 and the transmitter 20.

The communication between the receiver 50 and the transmitter 20 during the contact phase can take place, e.g., while recharging a battery of the transmitter 20. In that case, the receiver contact unit 70 may be implemented in a charging slot of the receiver 50, and the transmitter contact unit 75 may be implemented at a thereto corresponding location.

It is to be understood that the explanations as given for the transmitter 20 also apply to the other transmitters 30 and 40. The contact phase can be executed by means of the receiver contact unit 70 and corresponding transmitter contact units (not shown in FIG. 1) of the transmitters 30 and 40. However, in a preferred embodiment as indicated in FIG. 1, the receiver 50 comprises a receiver contact unit for each transmitter which can be physically inserted into the receiver 50 as a base station. In FIG. 1, the receiver 50 comprises the receiver contact unit 70 for the transmitter 20, a receiver contact unit 100 for the transmitter 30, and a receiver contact unit 110 for the transmitter 40.

What is claimed is:

1. A telemetry system comprising: a transmitter for providing a wireless data transmission with a receiver, wherein:
   the receiver comprises a receiver contact unit for providing a contact with a transmitter contact unit of the transmitter, whereby the receiver contact unit and the transmitter contact unit are adapted to provide data communication independent of the wireless transmission during a contact phase for assigning a transmission channel to the transmitter or to the receiver; and further wherein:
   the receiver further comprises means for monitoring transmission activity in a range of frequency channels for determining channels in use, and assigning the transmission channel to the transmitter in accordance with the determined channels in use.

2. The telemetry system according to claim 1, wherein the receiver is adapted to physically receive the transmitter as a base station.

3. The telemetry system according to claim 1, wherein the receiver comprises a synthesizer receiver unit for stepping through a predefined channel range and for measuring the received signal strength on each one of those channels.

4. The telemetry system according to claim 1, wherein the receiver contact unit and the transmitter contact unit respectively comprise corresponding components for establishing and providing—during the contact phase—a communication therebetween, whereby the communication can be unidirectional or bidirectional.

5. The telemetry system according to claim 1, wherein the receiver contact unit comprises one or more receiver contact areas, and the transmitter contact unit comprises one or more transmitter contact areas, which—when brought into contact—establish a direct contact therebetween.

6. The telemetry system according to claim 1, wherein the transmitter or the receiver contain means for making information visible.

7. The telemetry system according to claim 1, wherein the telemetry system is used for medical applications.

8. The telemetry system according to claim 7, wherein the medical applications include pulsoximetry.

9. The telemetry system according to claim 7, wherein the medical applications include electrocardiography.

10. A method for assigning transmission channels in a telemetry system comprising a transmitter for providing a wireless data transmission with a receiver the method comprises the steps of:
    monitoring transmission activity in the receiver in a range of frequency channels for determining channels in use; and
    during a contact phase, providing a data communication between the transmitter and the receiver independent of the wireless data transmission for assigning a transmission channel to the transmitter or to the receiver, wherein the receiver operates to assign the transmission channel to the transmitter in accordance with the determined channels in use.

11. The method according to claim 10, wherein the communication between the receiver and the transmitter during the contact phase takes place while recharging a battery of the transmitter.

12. A method for assigning transmission channels in a telemetry system comprising a transmitter for transmitting electromagnetic signals, and a receiver for receiving the signals from the transmitter, the method comprises a step of:
    during a contact phase, providing a data communication between the transmitter and the receiver for assigning a transmission channel to the transmitter or to the receiver,
    wherein—during the contact phase—the receiver further transfers to the transmitter: a unique transmitter identity code for the transmitter, or a receiver identity code of the receiver, or information about a standby mode of the transmitter or personal information about a person who will receive or carry the transmitter.

13. The method according to claim 12, wherein in case that the receiver has assigned and transferred a unique transmitter identity code for the transmitter:
    the transmitter transmits—during an operation thereof—the transmitter identity code and other data on the assigned channel to the receiver,
    the receiver performs a substantially ongoing check of the received transmitter identity code for determining whether a signal received by the receiver on the respective channel originates from the transmitter.

14. The method according to claim 10, wherein the transmitter is programmed to a specific channel and, during the contact phase, the transmitter operates to reprogram the receiver by indicating said specific channel as the channel to be used for communicating with the receiver.

15. A method for assigning transmission channels in a telemetry system comprising a transmitter for transmitting electromagnetic signals, and a receiver for receiving the signals from the transmitter, the method comprises a step of:
    during a contact phase, providing a data communication between the transmitter and the receiver for assigning a transmission channel to the transmitter or to the receiver,
    wherein the transmitter acknowledges a valid reception of received data from the receiver.

16. A telemetry system for use for medical applications, comprising: a transmitter for providing a wireless data transmission with a receiver, wherein:

the receiver comprises a receiver contact unit for providing a contact with a transmitter contact unit of the transmitter, whereby the receiver contact unit and the transmitter contact unit are adapted to provide data communication independent of wireless transmission during a contact phase for assigning a transmission channel to the transmitter or to the receiver; and further wherein:

the transmitter is programmed to a specific channel and, during the contact phase, the transmitter operates to reprogram the receiver by indicating said specific channel as the channel to be used for communicating with the receiver.

* * * * *